United States Patent [19]
Liu

[11] Patent Number: 5,626,811
[45] Date of Patent: May 6, 1997

[54] PROCESS OF MAKING A MONOFILAMENT

[75] Inventor: Cheng-Kung Liu, Norwalk, Conn.

[73] Assignee: United States Surgical Corporation, Norwalk, Conn.

[21] Appl. No.: 509,948

[22] Filed: Aug. 1, 1995

Related U.S. Application Data

[63] Continuation of Ser. No. 164,512, Dec. 9, 1993, abandoned.

[51] Int. Cl.⁶ .................. D01D 5/08; D01D 5/12
[52] U.S. Cl. .................. 264/210.7; 264/210.8; 264/211.14; 264/235.6
[58] Field of Search .................. 264/210.2, 210.7, 264/210.8, 211.14, 235.6, 290.5, 290.7

[56] References Cited

U.S. PATENT DOCUMENTS

| | | |
|---|---|---|
| 3,630,205 | 12/1971 | Listner . |
| 3,978,192 | 8/1976 | Sussman . |
| 4,052,988 | 10/1977 | Doddi et al. . |
| 4,243,775 | 1/1981 | Rosensaft et al. . |
| 4,300,565 | 11/1981 | Rosensaft et al. . |
| 4,440,789 | 4/1984 | Mattei et al. . |
| 4,559,945 | 12/1985 | Koelmel et al. . |
| 4,591,630 | 5/1986 | Gertzman et al. . |
| 4,643,191 | 2/1987 | Bezwada et al. . |
| 4,649,921 | 3/1987 | Koelmel et al. . |
| 4,653,497 | 3/1987 | Bezwada et al. . |
| 4,838,267 | 6/1989 | Jamiolkowski et al. . |
| 4,911,165 | 3/1990 | Lennard et al. . |
| 5,007,923 | 4/1991 | Bezwada et al. . |
| 5,047,048 | 9/1991 | Bezwada et al. . |
| 5,080,665 | 1/1992 | Jarrett et al. . |
| 5,217,485 | 6/1993 | Liu et al. . |
| 5,236,444 | 8/1993 | Muth et al. . |
| 5,294,395 | 3/1994 | Broyer .................. 264/178 F |

*Primary Examiner*—Leo B. Tentoni

[57] ABSTRACT

Monofilaments fabricated from polymers derived in whole or in part from p-dioxanone are provided. The monofilaments exhibit improved tensile properties such as straight-pull strength and knot-pull strength. The monofilaments can be employed in the fabrication of a wide variety of surgical devices such as sutures, fabric prostheses, and the like.

13 Claims, 2 Drawing Sheets

PROCESS OF MAKING A MONOFILAMENT

This application is a continuation of U.S. Ser. No. 08/164,512, filed Dec. 9, 1993, now abandoned.

BACKGROUND OF THE INVENTION

This invention relates to monofilaments fabricated from polymers derived in whole or in part from p-dioxanone and a method for producing such monofilaments, as well as to medical/surgical devices fabricated in whole or in part from such monofilaments. More particularly, this invention relates to poly-p-dioxanone monofilaments possessing increased straight-pull strength and knot-pull strength and to a method for producing such monofilaments which employs a cold draw process as well as to sutures, fabric prostheses, etc. fabricated in whole or in part from the monofilaments of this invention.

Monofilaments produced from polymers derived in whole or in part from p-dioxanone are known in the manufacture of medical/surgical articles such as sutures, fabric prostheses, and the like. See, e.g., U.S. Pat. Nos. 4,052,988, 4,243,775, 4,300,565, 4,440,789, 4,559,945, 4,591,630, 4,643,191, 4,649,921, 4,653,497, 4,838,267, 5,007,923, 5,047,048 and 5,080,665.

Methods for producing monofilaments from p-dioxanone-containing polymers are known and generally include the steps of extruding such a polymer to provide a monofilament, quenching the monofilament to effect its solidification, drawing/stretching the solidified monofilament at a suitable draw ratio before, during and/or after it has been heated to achieve molecular orientation and impart strength to the monofilament and, optionally, annealing the monofilament to relieve internal stresses. See, e.g., U.S. Pat. Nos. 4,052,988, 4,643,191 and 4,838,267.

SUMMARY OF THE INVENTION

It has been surprisingly discovered that if in a process for producing a monofilament of a p-dioxanone-containing polymer the solidified monofilament is drawn under ambient temperatures in the absence of applied heat (hereinafter referred to as cold (drawn), a monofilament is obtained which possesses increased tensile strength such as straight-pull strength and knot-pull strength compared to p-dioxanone containing monofilaments which are not cold drawn.

The monofilaments of this invention can be employed in the fabrication of a wide variety of medical/surgical devices such as monofilament and multifilament sutures, woven, knitted or braided fabric prostheses, and the like.

DESCRIPTION OF THE PREFERRED EMBODIMENTS

Figure 1:
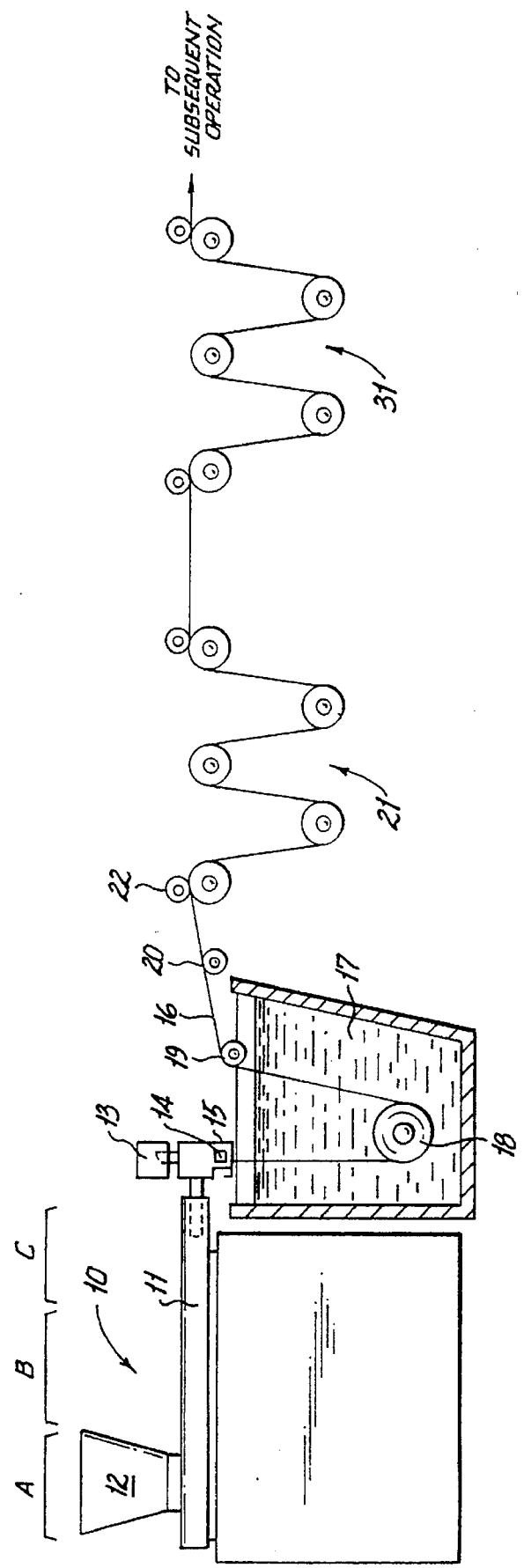
FIG. 1 is a schematic illustration of an apparatus which is suitable for carrying out the extruding, quenching and cold drawing steps of the monofilament manufacturing process of this invention.

FIG. 1 substantially illustrates the extruding, quenching and cold drawing operations of the monofilament manufacturing operation herein. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of polymer are introduced to the extruder through drier-hopper 12. Polymers which can be advantageously employed in the practice of this invention include polymers derived in whole or in part from p-dioxanone. The polymers can contain from about 80 to about 100 weight percent, preferably from about 92 to about 100 weight percent and most preferably from about 95 to about 100 weight percent p-dioxanone. The polymers can be homopolymers of p-dioxanone or copolymers derived from p-dioxanone and one or more other copolymerizable monomers such as glycolide, glycolic acid, lactide, lactic acid, epsilon-caprolactone, trimethylene carbonate, and their derivatives. Structurally, the polymers can be random, block or graft-type copolymers and possess linear or branched configurations. Similarly, polymeric blends obtained by blending two or more polymers at least one of which is derived in whole or in part from p-dioxanone can be employed in the practice of the present invention. Useful polymers will advantageously possess an inherent viscosity of from about 0.9 to about 3.5 dl/g when measured at 30° C. and at a concentration of 0.25 g/dl in hexafluoroisopranol (HFIP).

As FIG. 1 shows, motor driven metering pump 13 delivers melt extruded polymer at a constant rate to spin pack 14 and thereafter through a spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 cm. If desired, a chimney (not shown), or shield, can be provided to reduce the length of the air gap, e.g., from 1 to 10 cm, thereby isolating monofilament 16 from contact with air currents which might otherwise affect the cooling of the monofilament in an unpredictable manner. Monofilament 16 is passed through quench bath 17 around driven roller 18 and over idle rollers 19 and 20. Optionally, a wiper (not shown) may remove excess water from the monofilament as it is removed from quench bath 17. On exiting the quench bath the monofilament enters first godet station generally indicated at 21.

First godet station 211 is equipped with five individual godets around which monofilament 16 is wrapped. The first individual godet is equipped with nip roll 22 to prevent slippage which might otherwise result. Upon entering first godet station 21, monofilament 16 passes over the first godet, under the second godet, over the third godet, under the fourth godet and over the fifth godet. The fifth godet is likewise equipped with a nip roll.

Monofilament 16 passing from first godet station 21 is stretched to effect the molecular orientation of the polymer from which it is fabricated and thereby further increase the tensile strength of the monofilament. Stretching of monofilament 16 is effected by second godet station generally indicated at 31 positioned down-line from first godet station 21. Second godet station 31 rotates at a faster speed than first godet station 21 to provide the desired draw ratio. Monofilament 16 can be drawn at a draw ratio ranging from about 3:1 to about 10:1 and preferably from about 3.5:1 to about 5:1.

Surprisingly, it has been discovered that if monofilament 16 is first drawn at ambient temperature in the absence of applied heat a significant increase in tensile strength is obtained compared to the strength of monofilaments drawn in accordance with conventional "hot draw" methods in which heat is applied to the monofilament in the drawing operation. The cold draw operation is carried out under ambient conditions, namely, at temperatures ranging from about 10° to about 25° C. and preferably from about 20° to about 23° C. Monofilament 16 can be drawn through the open air or, optionally, through a suitable liquid medium that is maintained within the aforementioned temperature range. The resulting cold drawn monofilament possesses a significant increase in tensile strength as is disclosed more fully hereinbelow.

Figure 2:
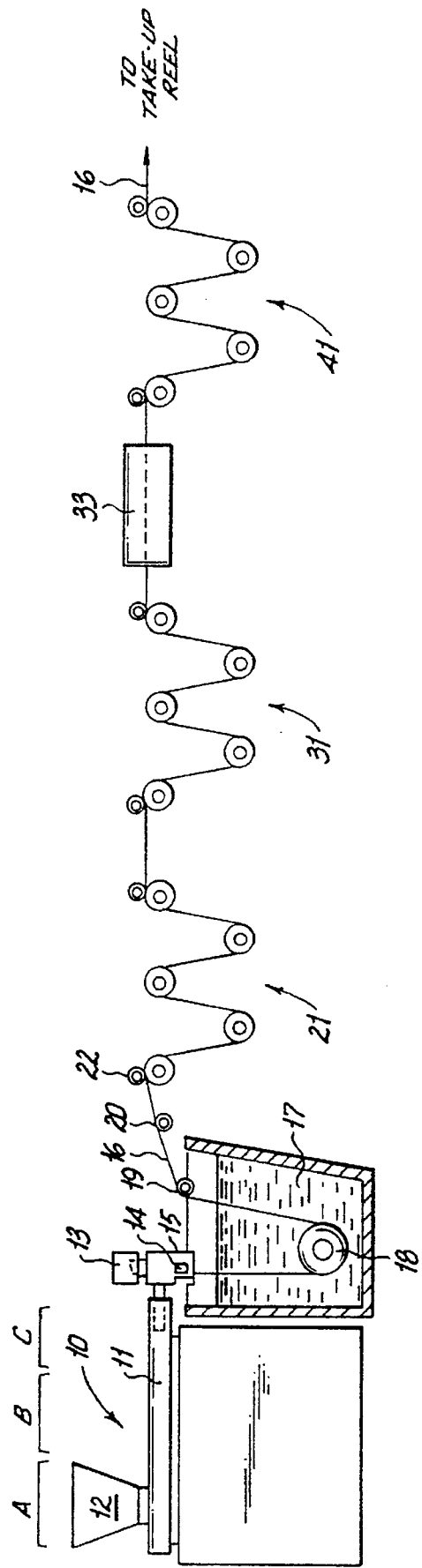
FIG. 2 is a schematic illustration of an apparatus which is suitable for carrying out the extruding, quenching, cold drawing and further processing operation of the monofilament manufacturing process of this invention.

Following the cold drawing operation, in accordance with methods that are known in the art, monofilament 16 optionally can be subjected to one or more further operations such as a second drawing operation or an annealing, cooling or equilibrating operation. For example, as shown more clearly in FIG. 2, monofilament 16 can be drawn a second time by drawing monofilament 16 through heating unit 33 by means of third godet station 41 which rotates at a faster speed than second godet station 31.

Monofilament 16 optionally can be subjected to an on-line annealing operation with or without relaxation as, e.g., by driving the monofilament through a second heating unit by a fourth godet station (not shown). For relaxation, the fourth godet station rotates at a slower speed than the third godet station thus relieving tension on the monofilament. It is to be understood that the on-line annealing operation can be carried out immediately after monofilament 16 has been cold drawn in accordance with the method of this invention. Alternatively, in the practice of this invention cold drawn monofilament 16 may be subjected to a second drawing operation before carrying out the annealing operation.

Static annealing can be carried out in accordance with the method described in U.S. Pat. No. 3,630,205. Thus, e.g., the monofilament may be wound around a creel and the creel placed in a heating cabinet maintained at a desired temperature, e.g., from about 40° to about 100° C. After a suitable period of residency in the heating cabinet, e.g., about 6 to 18 hours or so, the monofilament will have undergone essentially no shrinkage. Optionally, the creel may be rotated within the heating cabinet in order to insure uniform heating of the monofilament. Preferably, the heating cabinet may be of the circulating hot nitrogen type in which case uniform heating of the monofilament will be achieved without the need to rotate the creel. Thereafter, the creel is removed from the heating cabinet and when returned to room temperature, the monofilament is removed from the creel, conveniently by cutting the wound monofilament at opposite ends of the creel. The annealed monofilaments can then be employed as monofilament sutures, or fabricated into multifilament sutures or fabric prostheses.

Monofilament 16 can also be subjected to a cooling operation as, for example, by placing cold drawn monofilament 16 in a freezer at a temperature of from about 5° to about −15° C. The cooling operation can be carried out immediately after the cold drawing operation or after the second drawing operation. It is also contemplated that monofilament 16 be cooled after the monofilament has been annealed in accordance with known methods. After being removed from the freezer, monofilament 16 can then be annealed a second time.

Monofilament 16 optionally can be equilibrated in accordance with the method disclosed in U.S. Pat. No. 5,217,485 wherein the drawn monofilament is permitted to equilibrate, or "rest", prior to undergoing the annealing operation.

It is further within the scope of this invention to incorporate one or more medico-surgically useful substances into the present invention, e.g., those which accelerate or beneficially modify the healing process. Thus, e.g., the medical/surgical devices of this invention can carry one or more therapeutic agents to be deposited at the surgical repair site. The therapeutic agent can be chosen for its antimicrobial properties, capability for promoting tissue repair or reconstruction and/or new tissue growth. Antimicrobial agents such as a broad spectrum of antibiotics (gentamycin sulfate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the devices, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is contemplated that it may be desirable to dye the monofilaments of the present invention in order to increase visibility of the suture in the surgical field. Dyes known to be suitable for incorporation in sutures can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, sutures in accordance with the invention are dyed by adding up to about a few percent and preferably about 0.2% dye, such as D&C Violet No. 2 to the resin prior to extrusion.

The following examples illustrate the practice of the present invention:

EXAMPLE 1

Monofilaments fabricated from polydioxanone (viscosity of 1.73 dl/g measured at 30° C. and at a concentration of 0.25 g/dl in HFIP) were prepared employing the apparatus of FIG. 1. The manufacturing conditions were as follows:

| CONDITIONS OF MANUFACTURING MONOFILAMENT | |
|---|---|
| Process Conditions | |
| | Extrusion Operation |
| extruder screw, rpm | 1.2 |
| pump, rpm | 10.2 |
| driven roller, mpm | 3.9 |
| barrel temp., °C., zone A | 95 |
| barrel temp., °C., zone B | 128 |
| barrel temp., °C., zone C | 129 |
| clamp temp., °C. | 129 |
| adapter temp., °C. | 130 |
| pump temp., °C. | 132 |
| barrel melt temp., °C. | 128 |
| pump melt temp., °C. | 127 |
| spinneret melt temp., °C. | 127 |
| barrel pressure, psi | 1450 |
| pump pressure, psi | 500 |
| pump size, cc per revolution | 0.16 |
| diameter of spinneret orifices, mm | 1.25 |
| no. of spinneret orifices | 1 |
| quench bath temp., °C. | 18 |
| depth of driven roller, cm | 16.5 |
| | Cold |

CONDITIONS OF MANUFACTURING MONOFILAMENT

Process Conditions

| | Drawing Operation |
|---|---|
| first godet station, mpm | 4 |
| second godet station, mpm | 20 |
| draw ratio | 5:1 |
| draw temp, °C. | 23 |
| | Second Drawing Operation |
| third godet station, mpm | 26 |
| draw ratio | 1.3:1 |
| draw temp, °C. | 95 |
| | Annealing Operation |
| annealing temp., °C. | 85 |
| duration of annealing, hours | 6 |

EXAMPLE 2

Monofilaments fabricated from a random copolymer derived from 96 weight percent p-dioxanone and 4 weight percent lactide (viscosity of 1.99 dl/g measured at 30° C. and at a concentration of 0.25 g/dl in HFIP) were prepared employing the apparatus of FIG. 1. The manufacturing conditions were as follows:

CONDITIONS OF MANUFACTURING MONOFILAMENT

Process Conditions

| | Extrusion Operation |
|---|---|
| extruder screw, rpm | 1.1 |
| pump, rpm | 5.3 |
| driven roller, mpm | 4.0 |
| barrel temp., °C., zone A | 100 |
| barrel temp., °C., zone B | 165 |
| barrel temp., °C., zone C | 165 |
| clamp temp., °C. | 170 |
| adapter temp., °C. | 160 |
| pump temp., °C. | 170 |
| barrel melt temp., °C. | 161 |
| pump melt temp., °C. | 162 |
| spinneret melt temp., °C. | 162 |
| barrel pressure, psi | 1100 |
| pump pressure, psi | 500 |
| pump size, cc per revolution | 0.297 |
| diameter of spinneret orifieces, mm | 1.25 |
| no. of spinneret orifices | 1 |
| quench bath temp., °C. | 40 |
| depth of driven roller, cm | 5 |
| | Cold Drawing Operation |
| first godet station, mpm | 4.0 |
| second godet station, mpm | 16.6 |
| draw ratio | 4.2:1 |
| draw temp, °C. | 23 |
| | Second Drawing Operation |
| third godet station, mpm | 24 |
| draw ratio | 1.4:1 |
| draw temp, °C. | 90 |
| | Annealing Operation |
| annealing temp., °C. | 85 |
| duration of annealing, hours | 6 |

For comparative purposes, control monofilaments, i.e., Comparative Examples A and B, fabricated from the same polymers of Examples 1 and 2 were produced using the same manufacturing conditions presented above, however, the control monofilaments were drawn in accordance with conventional "hot drawing" procedures, i.e., the monofilaments were drawn through an oven at a temperature of 80° C.

The tensile properties of the monofilaments of Examples 1 and 2 and Comparative Examples A and B were measured on an Instron Tensile Tester (Instron Corp.) using the following procedures:

PROCEDURES FOR MEASURING TENSILE PROPERTIES OF MONOFILAMENTS

| Physical Property | Test Procedure |
|---|---|
| knot-pull strength, kg | U.S.P. XXI, tensile strength, sutures (881) |
| straight-pull strength, kg | ASTM D256-88, Instron Corporation |

The results of these tests are set forth in Table I as follows:

TABLE I

| (kpsi) | Straight-pull Strength (kpsi) | Knot-pull Strength |
|---|---|---|
| Example 1 | 95.6 | 50.0 |
| Comparative Example A | 85.5 | 43.3 |
| Example 2 | 77.8 | 41.1 |
| Comparative Example B | 49.1 | 29.8 |

As can be seen from the data in Table I, the monofilaments which were subjected to the cold drawing operation exhibited superior tensile properties relative to the monofilaments which were subjected to the hot drawing operation.

Obviously, modifications and variations of the present invention are possible in light of the above teachings. It is therefore to be understood that changes may be made in particular embodiments of the invention described which are within the full intended scope of the invention as defined by the claims.

What is claimed is:

1. A method of manufacturing a monofilament which comprises:

a) extruding and quenching a polymer derived in whole or in part from p-dioxanone to provide a solidified monofilament; and b) increasing the tensile strength of the monofilament by cold drawing the solidified monofilament, whereby the cold drawn monofilament has a higher tensile strength compared to a monofilament similarly processed except using only hot drawing.

2. The method of claim 1 wherein the polymer is selected from the group consisting of a homopolymer, copolymer and polymeric blend.

3. The method of claim 1 wherein the polymer comprises from about 80 to about 100 weight percent p-dioxanone.

4. The method of claim 1 wherein the polymer comprises from about 92 to about 100 weight percent p-dioxanone.

5. The method of claim 1 wherein the monofilament is cold drawn at a draw ratio ranging from about 3:1 to about 10:1.

6. The method of claim 1 further comprising the step of subjecting the cold drawn monofilament to one or more additional operations selected from the group consisting of drawing, annealing, cooling and equilibrating the monofilament.

7. The method of claim 1 wherein the monofilament is cold drawn at a temperature ranging from about 10° to about 25° C.

8. The method of claim 1 wherein the cold drawn monofilament is subjected to a subsequent drawing operation.

9. The method of claim 1 wherein the cold drawn monofilament is subjected to an annealing operation.

10. A method of manufacturing a monofilament which comprises:

a) extruding a polymer derived in whole or in part from p-dioxanone to provide a molten monofilament;

b) quenching the molten monofilament to provide a solidified monofilament;

c) cold drawing the solidified monofilament at a draw ratio ranging from about 3:1 to about 10:1 and a temperature ranging from about 10° to about 25° C.;

d) hot drawing the cold drawn monofilament; and, e) annealing the hot drawn monofilament to provide a monofilament exhibiting increased tensile strength properties relative to a monofilament which is fabricated from the same polymer and produced in accordance with conventional hot drawing procedures.

11. The method of claim 10 wherein the polymer is selected from the group consisting of a homopolymer, copolymer and polymeric blend.

12. The method of claim 10 wherein the polymer comprises from about 80 to about 100 weight percent p-dioxanone.

13. The method of claim 10 wherein the polymer comprises from about 92 to about 100 weight percent p-dioxanone.

* * * * *